United States Patent [19]

Howell

[11] 4,428,511

[45] Jan. 31, 1984

[54] FLUID HANDLING APPARATUS HAVING A FLUID METERING VOLUME THEREIN

[75] Inventor: Gary W. Howell, Newark, Del.

[73] Assignee: E. I. Du Pont de Nemours and Company, Wilmington, Del.

[21] Appl. No.: 296,850

[22] Filed: Aug. 27, 1981

[51] Int. Cl.³ ............................................. B65D 88/54
[52] U.S. Cl. ................................... 222/309; 222/481; 137/625.11; 137/624.18
[58] Field of Search ............... 222/372, 309, 386, 387, 222/478, 481, 484, 485, 486, 526, 532, 544, 548, 553, 251; 251/59, 60, 133, 134, 129; 137/625.46, 624.18, 625.11, 625; 403/353, 345, 11, 12, 348, 13; 248/646, 652, 658, 673, 678, 637

[56] References Cited

U.S. PATENT DOCUMENTS

| | | | |
|---|---|---|---|
| 1,854,370 | 4/1932 | Droege | 251/357 |
| 2,283,772 | 5/1942 | Stowe | 251/357 |
| 2,736,339 | 2/1956 | Asbury et al. | 137/625.46 |
| 2,864,039 | 12/1958 | Matthews | 251/133 |
| 3,124,162 | 3/1964 | Cameron | 137/625.11 |
| 3,233,629 | 2/1966 | Beck | 137/624.18 |
| 3,237,644 | 3/1966 | Beck et al. | 137/624.18 |
| 3,297,053 | 1/1967 | McKinney | 137/625.46 |
| 3,443,592 | 5/1969 | Felmlee | 137/625.11 |
| 3,454,784 | 7/1969 | Wantz et al. | 307/141 |
| 3,477,207 | 11/1969 | Auger | 55/197 |
| 3,542,071 | 11/1970 | Lightner et al. | 137/625.46 |
| 3,752,167 | 8/1973 | Makabe | 137/609 |
| 3,837,360 | 9/1974 | Bubula | 137/625.46 |
| 3,972,350 | 8/1976 | Pickett | 137/624.18 |
| 3,995,494 | 12/1976 | Muller et al. | 73/421.5 R |

*Primary Examiner*—Joseph J. Rolla
*Assistant Examiner*—Kenneth Noland

[57] ABSTRACT

A fluid handling device of the rotary slot type is characterized by a fluid metering volume disposed in the stator of the device in close proximity to a fluid transfer passage formed in the stator. The metering volume receives a piston movable in a suction and a pumping stroke to draw fluid into the metering volume and to pump fluid therefrom. A rotary seal having the slot formed therein is received by seal rotating actuator such that a portion of a tab formed on the seal is accessible to permit removal of the seal from the rotating actuator.

9 Claims, 7 Drawing Figures

4,428,511

FLUID HANDLING APPARATUS HAVING A FLUID METERING VOLUME THEREIN

BACKGROUND OF THE INVENTION

This invention relates to a fluid handling apparatus especially useful in connection with a device for automatically analyzing a sample of a fluid under test.

In a clinical device for automatically analyzing a sample of a liquid fluid under test to determine the presence of various chemicals therein, such as the Automatic Clinical Analyzer sold by E. I. du Pont de Nemours and Company, it is necessary to provide a fluid handling system adapted to select various ones of a plurality of chemical reagents and convey a metered quantity of a selected one of the reagents to successive portions of the sample. The fluid handling system used in conjunction with the Automatic Clinical Analyzer includes a piston pump combined with a stack valve such as that disclosed and claimed in U.S. Pat. No. 4,002,070 (Howell), assigned to the assignee of the present invention.

It is necessary that the fluid handling system exhibit certain basic requirements. First, the system must be able to accurately meter precise quantities of reagent and accurately deliver the metered quantity to a desired location. The time required for reagent metering and delivery has an effect upon the operating cost, both from the standpoint of machine usage efficiency and from the standpoint of reagent supply expense. Second, in any fluid handling system, care must be exercised so that carry over of reagent does not occur. That is, caution should be exercised to insure that a reagent applied through the pump and valve to a given location is purged from the fluid handling system before a different reagent is metered and delivered. Unless this precaution is taken the possibility exists that the results of various ones of the tests may be impaired due to contamination of a given portion of the sample by chemical reagent utilized in connection with a test performed on a previous portion of the sample. It should be recognized that the same considerations of machine usage efficiency and purging fluid supply cost apply during a purging cycle as during a reagent delivery cycle.

A rotary valve is a device which is adapted to interconnect and to supply a fluid (either liquid or gas) from a single fluid source or from a plurality of fluid sources respectively to a plurality of user destinations or to a single user destination. Exemplary of a rotary valve are those devices disclosed in U.S. Pat. No. 3,752,167 (Makabe), U.S. Pat. No. 3,837,360 (Bubula), U.S. Pat. No. 3,542,071 (Lightner et al.), U.S. Pat. No. 3,443,592 (Felmlee), U.S. Pat. No. 3,237,644 (Beck et al.), U.S. Pat. No. 3,233,629 (Beck), U.S. Pat. No. 3,477,207 (Auger), U.S. Pat. No. 3,972,350 (Pickett) and U.S. Pat. No. 3,297,053 (McKinney). U.S. Pat. No. 3,474,784 (Wantz et al.), U.S. Pat. No. 3,995,494 (Muller et al.) and U.S. Pat. No. 3,124,162 (Cameron) disclose selector valve devices. Because of its ability to interconnect various fluid sources with various user locations a rotary slot valve may have utility in a fluid handling system for an automatic clinical analysis device. In addition, if the valve were configured to include a fluid metering chamber therein increased machine efficiency and reduced reagent usage would appear to be achievable.

A rotary slot valve generally includes a stationary stator member against the upper surface of which a valve seal member is rotatably disposed. Fluid communication between selected ones of fluid passages disposed in the stator is permitted through a slot provided in the rotating seal member while the other nonselected passages in the stator are isolated by the remainder of the seal member. However, as with any relatively moving contacting surfaces, friction and wear occurs. Thus, over a period of time it is possible that periodic replacement of the rotating seal member may be required. This activity requires a finite amount of time to accomplish and should be minimized in order to maximize machine usage efficiency.

In view of the foregoing it is believed advantageous to provide a fluid handling apparatus of the rotary slot type which is provided with a fluid metering chamber proximal to fluid passages provided therein. It is also believed advantageous to provide a positive displacement pump member movable within the metering chamber to draw fluid into the chamber and pump fluid therefrom. In addition, it is believed advantageous to provide a fluid handling apparatus of the rotary slot type in which the relatively moving rotary member may be expeditiously changed without the requirement of any tools to thus further maximize machine usage efficiency.

SUMMARY OF THE INVENTION

The instant invention relates to a fluid handling apparatus of the rotary slot type which includes a stator member having a plurality of fluid conduction passages, a fluid transfer passage, and a fluid metering chamber formed therein. One end of each of the fluid conduction passages and of the fluid transfer passage opens onto a planar surface provided on the stator. A piston is slidably disposed in a close fitting relationship within the fluid metering volume. A rotating seal member having a slot formed therein is rotatably disposed with respect to the planar surface of the stator. The seal member is provided with a slot sized to permit communication between the transfer passage and one of the conduction passages. A rotary actuator such as a stepping motor is connected to the seal member for moving the same from a first position in which the transfer passage communicates through the slot with one of the conduction passages to a second position in which the transfer passage communicates through the slot to a second of the conduction passages. A linear actuator is connected to the piston for moving the same in a first, suction, direction when the seal is in the first position to draw fluid into the metering chamber and for moving the piston in a second, pumping, direction when the seal is in the second position to positively displace fluid from the metering volume into the second conduction passage.

The stator is provided with an arm having a slot therein. The rotary actuator has a pin arranged thereon such that when the rotary actuator is moved in a first direction the pin is engaged within the arm to secure the rotary actuator to the stator. Movement of the rotary actuator in a counter direction disengages the pin from the stator. The seal member is provided with a projecting tab which is receivable within an appropriately sized cut out portion provided in the rotary actuator shaft. When the seal is received within the cut out portion of the shaft the tab is accessible for manipulation by the operator to permit the seal to be removable from the plunger. The removability of the rotary actuator from the stator and the seal member from the rotary actuator permits the seal member to be quickly and expeditiously replaced without the need of tooling.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
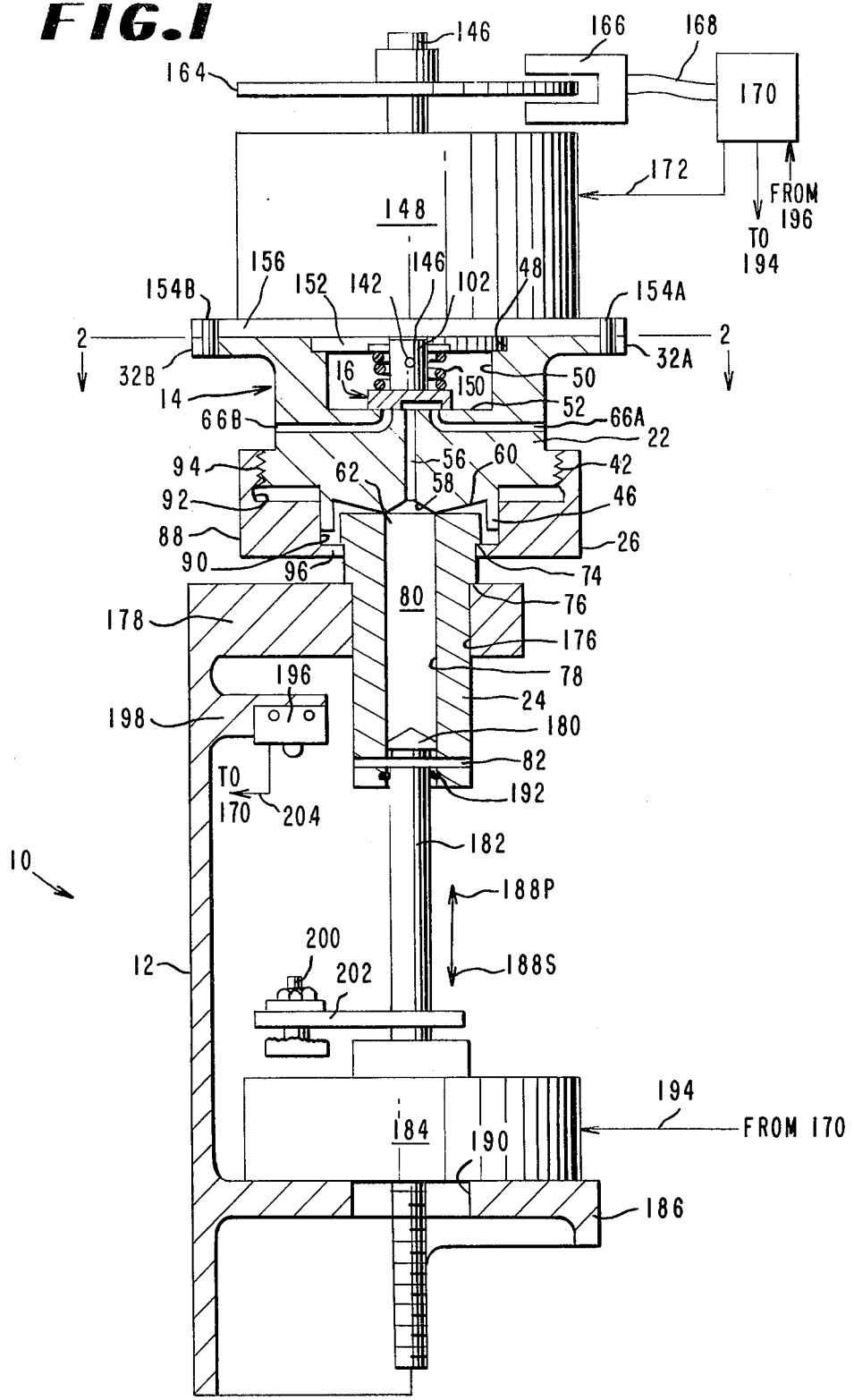
FIG. 1 is an elevational view entirely in section of a fluid handling apparatus in accordance with the instant invention.

Throughout the following detailed description similar reference numerals refer to similar elements in all figures of the drawings.

With reference to FIG. 1 shown is a side elevational view entirely in section of a fluid handling apparatus generally indicated by reference character 10. The fluid handling apparatus 10 is supported on a suitable bracket 12 which may be affixed to any predetermined support surface.

The fluid handling apparatus 10 includes a stator member indicated by a reference character 14 and a rotatably movable rotary seal member 16 supported for rotational movement with respect to the stator 14.

The stator 14 includes a generally cylindrical valve body portion 22, an elongated reservoir or metering cylinder structure portion 24, these last two elements being threadedly interconnected by a collar 26. Although the stator 14 in FIG. 1 is shown as configured from the discrete valve body portion 22, metering cylinder structure portion 24 and collar 26, it should be understood that the stator 14 may be formed in the manner illustrated in FIG. 7 in which the body portion 22' and the metering cylinder structure portion 24' are integrally formed. Such a construction obviates the need for a collar.

Figure 2:
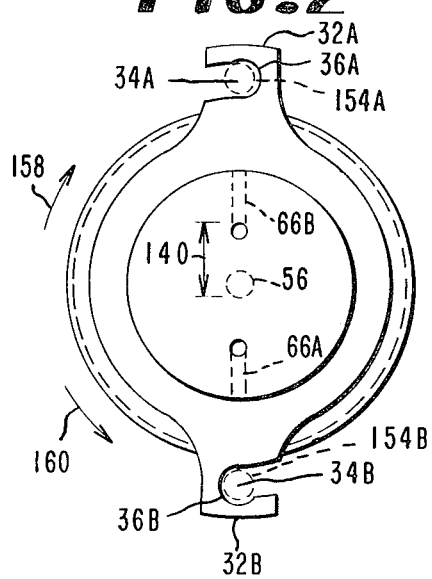
FIG. 2 is a sectional view taken along section lines 2—2 of FIG. 1.

The valve body portion 22 is a generally cylindrical member formed of a suitable material having a lubricating tendency when another member is frictionally abraded thereagainst. Suitable for use as the material used to form the body 22 is an acetal resin material sold by E. I. du Pont de Nemours and Company under the trademark Delrin ®. Preferably, off center stock is utilized to avoid porosity. Of course, other suitable materials such as TFE-fluorocarbon resin or nylon may also be used to form the valve body 22. A pair of opposed arms 32A and 32B extends radially outwardly from the upper end of the valve body 22. The arms 32 are provided with oppositely facing slots 34A and 34B (FIG. 2), each of the slots respectively terminating in a notch 36A and 36B for a purpose hereafter disclosed.

The lower exterior surface of the body portion 22 is provided with threads 42. An annular retainer sleeve 46 depends downwardly from the lower surface of the valve body 22. The valve body 22 is provided with a counterbore region 48 formed in the upper surface thereof to define a keyway for a purpose hereafter discussed. A second bored region 50 extends coaxially with the first counterbore 48 and terminates in a generally planar surface 52. A central axial throughbore 56 is provided within the valve body 22 to define a fluid transfer passage through the stator 22. The fluid transfer passage 56 terminates in a frustoconical surface 58. An annular surface 60 is defined between the radially outer edge of the frustoconical surface 58 and extends radially outwardly to the base of the sleeve 46. The surface 60 is inclined at a predetermined angle (typically about three degrees) to define a substantially annular rim 62 about the frustoconical surface 60.

At least two but preferably a plurality of fluid conduction passages 66 are provided within the valve body 22. Of course, any suitable number of fluid conduction passages 66 as are necessary may be conveniently provided in the valve body portion 22. However, for clarity of illustration, two of the fluid conduction passages 66A and 66B are visible in the section view shown in FIG. 1. The flow passages 66 extend from the cylindrical surface of the valve body 22 intermediate the threads 42 and the arms 32 and open on the flat surface 52 at the base of the counterbore 50. The fluid conduction passages 66, as well as the fluid transfer passage 56, are formed with smooth, noncreviced, continuous sidewalls so that fluid conducted or transferred therethrough is not afforded an opening in which to remain. Thus, carry over is minimized.

The metering cylinder structure 24 is an elongated cylindrical member having a first and a second annular shoulder 74 and 76 formed therein respectively adjacent the upper and intermediate portions of the exterior thereof. The member 24 is formed of a suitable material, as stainless steel, although other suitable material, such as acetal resin material sold by E. I. du Pont de Nemours and Company under the trademark Delrin ® may be used. If the stator 14 is formed with an integral valve body 22' and metering cylinder structure 24' (FIG. 7), the acetal resin material such as Delrin ® is preferred. It should be noted that forming the stator 14 in a manner in which the body 22' and the metering cylinder structure 24' are integral provides the advantage of reduced mill costs. In addition, such an integral structural arrangement further minimizes the possibility of fluid carry over.

A throughbore 78 having a diameter substantially equal to the diameter of the frustoconical surface 58 in the valve body 22 extends through the member 24. The bore 78 can vary in size (diameter and length) consistent with the application to thereby meter appropriately sized volumes of fluid. The bore 78 is formed of smooth, noncreviced, continuous sidewalls for the reason discussed above. The outside diameter of the upper portion of the member 24 between the flat top surface thereof and the first shoulder 72 formed thereon is sized to be snuggly received within the downwardly depending sleeve 46 provided on the valve body 22. When so conjoined the rim 62 on the valve body 22 mates against the upper surface of the member 24 adjacent the bore 78 and the body 22 and member 24 cooperate to define a fluid metering volume 80 therein. When the valve body 22 and the member 24 are so conjoined the fluid transfer passage 56 is in fluid communication and coaxially aligned metering volume 80. The lower end of the member 24 is provided with a radially extending backflush passage 82 communicating with the metering volume 80.

The valve body 22 and the member 24 are held in the described assembled relationship by the collar 26. The collar 26 includes a generally cylindrical central portion 88 having a cylindrical bore 90 formed therein. The bore 90 is coaxial with the passage 56 and the bore 78 and exhibits a dimension substantially equal to the dimension of the sleeve 46 depending downwardly from the body portion 22. The collar 26 is counterbored as at 92 to define an upwardly extending annular region having threads 94 provided therein. The bore 90 is partially closed by radially inwardly extending annular portion 96 having a diameter substantially equal to the diameter of that portion of the member 24 intermediate the shoulders 74 and 76. The stator 12 is formed by threadedly interconnecting the threads 94 on the collar 26 with the threads 42 on the lower portion of the valve body 22 until the annular region 96 adjacent the lower end of the collar 26 is brought into an abutting relationship with the undersurface of the shoulder 74 formed on the member 24.

Figure 4:
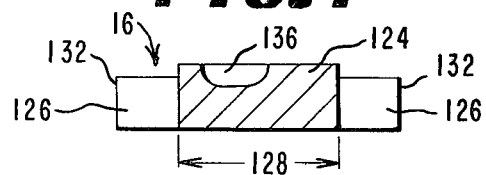
FIG. 4 is a section view of the seal member taken along section lines 4—4 of FIG. 3.
Figure 6:
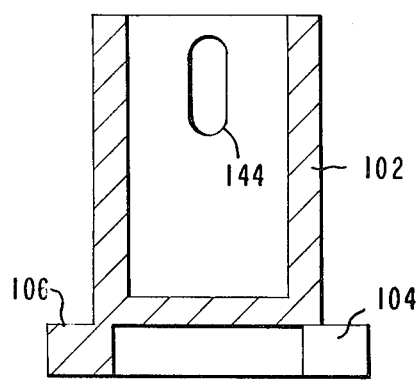
FIG. 6 is a section view of the plunger taken along section lines 6—6 of FIG. 5.
Figure 5:
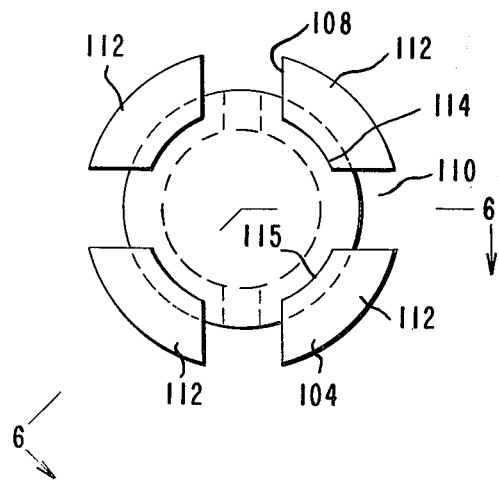
FIG. 5 is a bottom view of a seal support plunger.

The rotary valve seal member 16 (FIGS. 3 and 4) is formed of an elastomeric material such as a fluroelastomer material sold by E. I. du Pont de Nemours and Company under the trademark Viton ®. The seal is removably mountable to a plunger member 102 (FIGS. 5 and 6). The plunger 102 is a hollow tubular member having an annular flange 104 connected to the lower end thereof. The flange 104 has a generally planar annular surface 106 thereon. The flange 104 is provided with cutouts 108 which cooperate to define a plurality of radially extending channels 110 defined between an array of feet 112.

Figure 3:
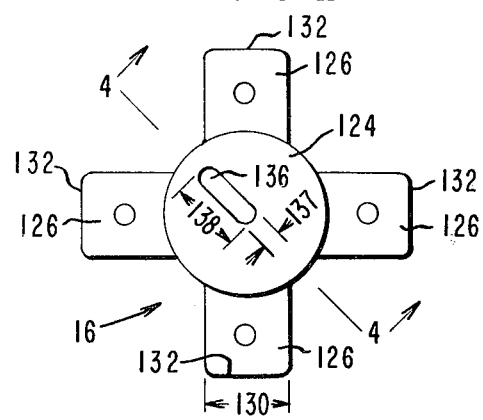
FIG. 3 is a view of the underside of the rotating seal member.

The rotary seal member 16 includes a central cylindrical body portion 124 (FIGS. 3 and 4) having a plurality of radially outwardly extending tabs 126 thereon. The diametrical dimension 128 of the body portion 124 and the width dimension 130 of the tabs 126 are sized to be respectively received within the cylindrical surface 115 provided on the radially inside edges of the feet 112 and within the channels 110 respectively. When so assembled the radially outward end 132 of each of the tabs 126 extends a predetermined distance past the outer diameter of the feet 112 so that the rotary seal 16 may be manipulated and manually inserted and removed by an operator. The central portion 124 of the seal 16 is provided with a substantially radially extending slot 136 having a predetermined slot width 137 (FIG. 3). The dimension of the slot width 137 is sized in accordance with the angular distance between the openings of adjacent fluid conduction passages 66 on the surface 52. The radial dimension 138 of the slot 132 is sufficient to encompass the radial distance 140 (FIG. 2) (including the dimensions of the openings) between the fluid transfer passage 56 and any one of the fluid conduction passages 66 terminating on the planar surface 52 of the valve body 22. The diametric dimension 128 of the rotary seal 120 is preferably any dimension up to 0.30 inch. This dimension size serves to reduce the friction generated between the rotary seal 120 and the surface 52 of the stator 14, thus reducing the torque required to rotate the seal 120. The radial dimension 138 of the slot 136 may be up to 0.10 inch. The radial dimension 138 and the slot width 137 are selected to reduce the volume of fluid which must be purged from the fluid handling device.

The plunger 102 is secured as by a pin 142 (FIG. 1) press fit into the depending shaft 146 of a rotary actuator 148. The pin 142 extends through an opening 144 provided in the plunger 102. Suitable for use as the rotary actuator 148 is a stepping motor such as that sold by Eastern Air Devices under model name Sigma. A spring 150 trapped between the rotary actuator 148 and the surface 106 on the plunger 102 biases the seal member 16 toward the stator 14. The spring 150 is sized to generate a sealing force to urge the seal member 16 against the surface 52. However, the sealing force is not large enough to create excessive wear.

The rotary actuator 148 has a generally cylindrical portion 152 which is sized to be closely received within the counterbore region 48 in the valve body 22. Downwardly depending positioning pins 154 extend from a face plate 156 of the rotary actuator 148. When the rotary actuator 148 is received within the counterbore 48 and the rotary actuator 148 is rotated in a first direction 158 (FIG. 2) the pins 154 thereon are received within the openings 34 on the arms 32 of the valve body 22. The arms 32 are resiliently urged outwardly and thereafter closed upon the downwardly depending pins 154 to thereby secure the same into the recesses 36 provided in the arms 32. Thus, the rotary actuator 148 is removably but firmly secured to the stator 12. Rotation of the rotary actuator 148 in a direction 160 counter to the direction 158 serves to disengage the rotary actuator 148 from the stator 14.

The upwardly projecting portion of the shaft 146 of the rotary actuator 148 is provided with an encoder wheel 164 operative to provide an indication of the relative position of the slot 136 in the rotary seal member 16 with respect to the planar surface 52 of the stator 12. The position indicia on the wheel 164 is read by any suitable device 166 and signals representative thereof applied on lines 168 to a controller 170. The controller 170 may typically take the form of a microprocessor operating under control of a program. Control signals are applied to the rotary actuator 148 on a line 172. In response to signals applied on the line 172 the shaft 146 is rotated in equiangular steps to thereby rotatably move the seal 16 across the flat planar surface 52 of the stator 12. The rotary actuator 148 is arranged to rotate the seal member 16 attached thereto from a first position in which the slot 136 permits communication between one of the fluid conduction passages 66A and the fluid transfer passage 56 to a second position in which the fluid transfer passage communicates with the second of the fluid conduction passage 66B.

In the embodiment of the invention shown in FIG. 1, the conjoined assembly of the stator 14, rotary seal 16, and rotary actuator 148 are receivable within an opening 176 provided through an arm 178 formed integral with the bracket 12. The metering cylinder portion 24 extends through the opening 176 and an abutment is formed between the shoulder 76 on the member 24 and the periphery of the opening 176 in the arm 178.

The fluid metering volume 80 formed in the stator 12 receives a piston 180 carried at the upper end of an elongated shaft 182 of a linear actuator 184. The linear actuator 184 is suitably supported on an outwardly depending shelf 186 integral with the bracket 12. The shaft 182 is displaceable upwardly in a pumping stroke 188P and downwardly in a suction stroke 188S, the directions 188 being parallel to the axis of the metering volume 80. Clearance for the shaft 182 is provided by a cutout 190 provided in the shelf 186. The shaft 182 is sealed as it enters the member 24 by an O-ring gasket 192. Control signals to the linear actuator 184 from the controller 170 are carried on a line 194. The position of the piston 180 within the metering volume 80 is monitored by a sensor 196 mounted to a shelf 198 of the bracket 12. A projecting pin 200 is attached to the shaft 182 by a connector 202. When the pin 200 engages the sensor 196 a signal representative of that occurrence is transmitted to the controller 170 on a line 204.

Figure 7:
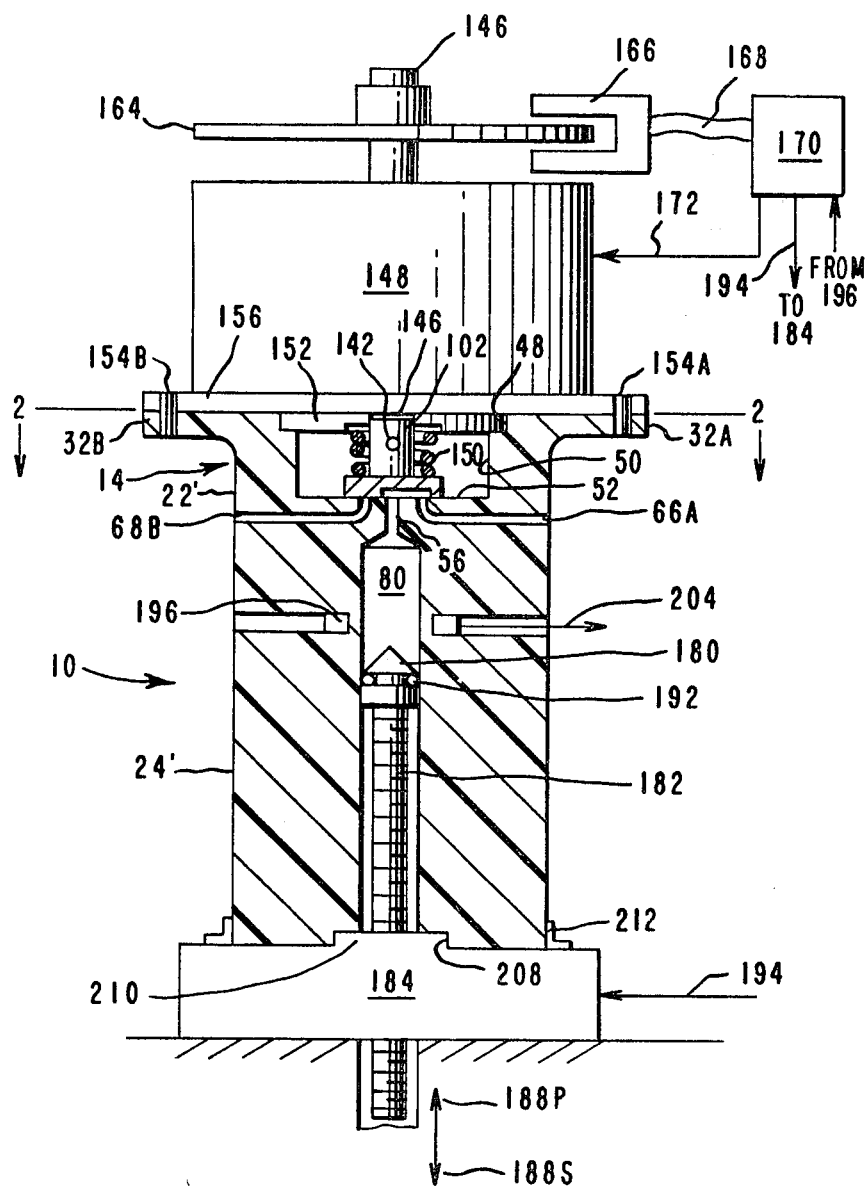
FIG. 7 is an elevational sectional view similar to FIG. 1 showing an alternate embodiment of the invention.

In the alternate embodiment of the invention shown in FIG. 7, the lower end of the metering cylinder portion 24' of the stator 14 is provided with a recess 208 which receives a fitting 210 on the actuator 184. In this manner the linear actuator 184 may be directly connected to the stator 14 thereby eliminating the requirement of the bracket 12 and compressing the vertical dimension of the fluid handling device 10. If desired, connectors 212 may be used to further secure the linear actuator 184 to the stator 14.

In operation, with the rotary seal member 16, in the first position, fluid communication may be established from a point (as a fluid source) external to the valve 10 through the fluid conduction passage 66A, the slot 136, the fluid transfer passage 56 to the fluid metering volume 80. The linear actuator 184 then draws the piston 180 in a suction stroke 188S to draw a predetermined volume of fluid into the volume 80. The rotary actuator 148 then rotates the seal member 16 to the second position in which communication between the fluid transfer passage 56 and the second fluid conduction passage 66B is established. The linear actuator 184 displaces the piston 180 in a pumping direction 188P, thus positively displacing the fluid within the volume 80 through the transfer passage 56, the slot 136 and the conduction passage 66B to a point external to the apparatus 10.

Those skilled in the art, having the benefits of the teachings of the instant invention as hereinabove set forth may effect numerous modifications thereto. These modifications are to be construed as lying within the scope of the instant invention, as defined in the appended claims.

What is claimed is:

1. A fluid handling apparatus comprising:
a stator having a planar surface, a first and a second fluid conduction passage, a fluid transfer passage and a fluid metering volume therein, one end of each of the conduction passages and of the transfer passage opening at the planar surface, the other end of the transfer passage communicating with the metering volume, the stator having a slotted arm thereon;
a piston disposed in a close fitting sliding relationship within the fluid metering volume;
a seal member having a slot formed therein, the seal being rotatably disposed with respect to the planar surface of the stator, the slot being sized to permit communication between the transfer passage and one of the conduction passages;
means connected to the seal for rotating the seal member from a first position in which the transfer passage communicates through the slot with the first of the conduction passages to a second position in which the transfer passage communicates through the slot with the second of the conduction passages, the seal rotating means having a positioning pin therein; and
an actuator connected to the piston for moving the piston in a first, suction, direction when the seal is in the first position to draw fluid through the first conduction passage, the slot and the transfer passage into the metering volume and for moving the piston in a second, pumping, direction when the seal is in the second position to urge fluid from the metering volume, through the transfer passage, the slot into the second conduction passage,
the rotating means being movable in a first direction wherein the positioning pin is engaged within the slotted arm to secure the rotating means to the stator and movable in a second direction wherein the positioning pin is disengaged from the slotted arm to permit removal of the rotating means from the stator.

2. The fluid handling apparatus of claim 1 further comprising a plunger member secured to the seal rotating means, the seal member being removably connectable to the plunger.

3. The fluid handling apparatus of claim 2 wherein the seal member has a tab formed thereon and wherein the plunger has a cutout portion formed therein, the cutout portion being sized to receive the seal member such that when the seal is received by the plunger a portion of the tab is accessible for manipulation to permit the seal to be removable from the plunger.

4. The fluid handling apparatus of claim 1 wherein the seal member has a tab formed thereon and wherein the rotating means has a cutout portion formed therein, the cutout portion being sized to receive the seal member such that when the seal is received by the rotating means a portion of the tab is accessible for manipulation to permit the seal to be removable from the rotating means.

5. The fluid handling apparatus of claim 1 wherein the portions of the conduction passages, the transfer passages and the metering volume in which and through which fluid flows are smooth and continuous so that fluid conducted through the passages and in the volume is not afforded a location in which to remain.

6. The fluid handling apparatus of claim 1 wherein the actuator is connected to the stator.

7. A fluid handling device comprising:
a stator having a planar surface, at least two fluid passages terminating at the planar surface, and an arm having a slot therein;
a seal member having a slot therein, the seal being rotatably disposed with respect to the surface of the stator;
means connected to the seal for rotating the same with respect to the planar surface to alternatively isolate the passages from each other or to permit communication between the passages through the slot in the seal member,
the rotating means having a pin thereon, the rotating means being movable in a first direction wherein the pin is engaged within the slotted arm to secure the rotating means to the stator and movable in a second direction wherein the pin is disengaged from the slotted arm to permit removal of the rotating means from the stator.

8. A fluid handling device of claim 7 wherein the seal member has a tab thereon and the rotating means has a cutout portion formed therein, the cutout portion being sized to receive the seal member such that when the seal is received by the rotating means a portion of the tab is accessible for manipulation to permit the seal to be removable from the rotating means.

9. A fluid handling device comprising:

a stator having a planar surface with at least two fluid passages terminating at the planar surface, and an arm with a slot therein;

a seal member having a slot therein, the seal being rotatably disposed with respect to the surface of the stator; and means connected to the seal for rotating the same with respect to the planar surface to alternately isolate the passages from each other or to permit communication between the passages through the slot in the seal member, the rotating means having a pin thereon, the seal having a tab thereon and the rotating means having a cutout portion formed therein, the cutout portion being sized to receive the seal such that when the seal is received by the rotating means, a portion of the tab is accessible for manipulation to permit the seal to be removable from the rotating means, the rotating means being movable in a first direction wherein the pin is engaged within the slotted arm to secure the rotating means to the stator and movable in a second direction wherein the pin is disengaged from the slotted arm to permit removal of the rotating means from the stator.

* * * * *